(12) United States Patent
Ghabrial et al.

(10) Patent No.: US 7,618,815 B2
(45) Date of Patent: Nov. 17, 2009

(54) VIRAL VECTORS USEFUL IN SOYBEAN AND METHODS OF USE

(75) Inventors: Said Ghabrial, Lexington, KY (US); Chunquan Zhanag, Ames, IA (US); Hongcang Gu, Chestnut Hill, MA (US)

(73) Assignee: University of Kentucky Research Foundation, Lexington, KY (US)

(*) Notice: Subject to any disclaimer, the term of this patent is extended or adjusted under 35 U.S.C. 154(b) by 316 days.

(21) Appl. No.: 11/370,175

(22) Filed: Mar. 8, 2006

(65) Prior Publication Data

US 2007/0214518 A1    Sep. 13, 2007

(51) Int. Cl.
  *C12N 15/00*   (2006.01)
  *A01H 1/00*    (2006.01)
  *C12N 15/82*   (2006.01)
  *C12N 15/87*   (2006.01)

(52) U.S. Cl. .................. 435/320.1; 800/278; 800/285

(58) Field of Classification Search ............. None
  See application file for complete search history.

(56) References Cited

U.S. PATENT DOCUMENTS 5,874,087 A    2/1999   Lomonossoff et al.
6,392,121 B1   5/2002   Mason et al.
6,559,359 B1   5/2003   Laten
6,884,623 B1   4/2005   Lomonossoff et al.

FOREIGN PATENT DOCUMENTS

WO    WO 98/36083    8/1998

OTHER PUBLICATIONS

Zhang et al. Oct. 2005 Virology 344:401-411.*
Choi et al. 2000, The Plant Journal 23:547-555.*
K. Gopinath et al., "Engineering Cowpea Mosaic virus RNA-2 into a Vector to Express Heterologous Proteins in Plants", Virology 267, 159-173 (20000.
Hongcang Gu, Said A. Ghabrial, "The Bean pod mottle virus proteinase cofactor andputative helicase are symptom severity determinants", Virology 333 (2005) 271-283.

* cited by examiner

*Primary Examiner*—Ashwin Mehta
*Assistant Examiner*—Li Zheng
(74) *Attorney, Agent, or Firm*—McDermott Will & Emery LLP

(57) ABSTRACT

The invention provides Bean pod mottle virus (BPMV) vectors useful for expression of heterologous proteins in plants such as soybean. The BPMV vectors are also useful for virus-induced gene silencing. The invention also provides methods for expressing a heterologous polypeptide in a plant such as soybean. The invention additionally provides methods for virus-induced gene silencing, particularly in a soybean plant, which can be used to determine the function of a gene of interest.

18 Claims, 7 Drawing Sheets

US 7,618,815 B2

VIRAL VECTORS USEFUL IN SOYBEAN AND METHODS OF USE

BACKGROUND OF THE INVENTION

This invention relates generally to the area of plant molecular biology and more specifically to plant viral expression vectors.

Plant virus-based vectors for expressing heterologous proteins in plants present promising biotechnological tools to supplement conventional breeding and transgenic technology. Considering the speed with which a virus infection becomes established throughout the plant and the high yield of viral-encoded proteins that accumulate in plants, the use of viral vectors provides an attractive and cost effective means for the overproduction of valuable proteins in plants and for rapid evaluation of new traits.

Several different types of positive sense RNA plant viruses have been developed as vectors for production of recombinant proteins and peptides (Pogue et al., *Annu. Rev. Phytopathol.* 40:45-74 (2002); Scholthof et al., *Annu. Rev. Phytopathol.* 34:299-323 (1996)). Depending on the structure of the viruses involved and their genome replication and expression strategies, a number of approaches including gene replacement, gene insertion, epitope presentation, and complementation have been utilized. Plant viral vectors are presently available for recombinant protein expression in a wide range of host plants including *Nicotiana benthamiana*, tobacco, squash, cucumber, wheat, barley, cowpea, *Nicotiana clevelandii*, *Chenopodium quinoa*, and *Arabidopsis* (Allison et al., *J. Virol.* 62:3581-3588 (1998); Brisson et al., *Nature* 310:511-514 (1984); Choi et al., *Plant J.* 23:547-555 (2000); Constantin et al., *Plant J.* 40:622-631 (2004); Dolja et al., *Proc. Natl. Acad. Sci. U.S.A.* 89:10208-10212 (1992); Fernandez-Fernandez et al., *Virology* 280:283-291 (2001); French et al., *Science* 231:1294-1297 (1986); Gopinath et al., *Virology* 267:159-173 (2000); Hagiwara et al., *J. Virol.* 73:7988-7993 (1999); Haupt et al., *Plant Physiol.* 125:209-218 (2001); Lacomme et al., *Plant J.* 34:543-553 (2003); Turnage et al., *Plant J.* 30:107-117 (2002)). Even with these advances, there are only a limited number of plant viral vectors that are suitable for systemic expression of foreign proteins in major crops like soybean. Soybean is a main source of oil and high-quality protein worldwide, and there is critical need for tools that allow for rapid evaluation of new traits involving expression of valuable proteins that confer disease/pest resistance and/or those that enhance the commercial value of soybean.

Thus, there exists a need for reagents useful for expressing heterologous proteins in plants such as soybean and determining the function of plant genes. The present invention satisfies these needs and provide related advantages as well.

SUMMARY OF INVENTION

The invention provides Bean pod mottle virus (BPMV) vectors useful for expression of heterologous proteins in plants such as soybean. The BPMV vectors are also useful for virus-induced gene silencing. The invention also provides methods for expressing a heterologous polypeptide in a plant such as soybean. The invention additionally provides methods for virus-induced gene silencing, particularly in a soybean plant, which can be used to determine the function of a gene of interest.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows the genome organization of BPMV RNA2 and vector construction strategy. RNA2 is translated into two overlapping carboxy coterminal polyproteins. CR, RNA2 replication cofactor; MP, movement protein; L-CP, large coat protein; S-CP, small coat protein. A foreign gene (GFP) is inserted between MP and L-CP coding sequences. The cleavage site (QM; boxed) is duplicated with the 8 C-terminal amino acids of the MP and the 19 N-terminal amino acids of the L-CP included for efficient processing. Amino acids, in the one-letter code, (SEQ ID NO: 1), are indicated above the nucleotide sequences (SEQ ID NO: 26, SEQ ID NO: 27 and SEQ ID NO: 28). Altered nucleotides are printed in red in lowercase. The GFP gene is shown as a green box. The introduced restriction sites, SwaI and AatII, are boxed. FIG. 1B shows a schematic presentation of BPMV RNA2 vector constructs. The upper sequence shows construct pGG7R2-GFP with GFP inserted between two artificial proteolytic cleavage sites; the designation G7R2 indicates that RNA2 was derived from BPMV strain G7. The lower sequence shows construct pGG7R2-V, which is a modified version of construct pGG7R2-GFP, contains additional restriction sites for cloning of foreign genes. A foreign gene can be cloned as a BamHI-MscI fragment in the pGG7R2-V vector after the vector is digested with same two enzymes. Alternatively, the foreign gene can be blunt-end ligated into MscI-digested pGG7R2-V vector. FIG. 1C shows a diagrammatic representation of the proteins expressed from the BPMV RNA2 vector listed in increasing order of their sizes: P19, Tomato bushy stunt virus P19 protein; Bar, phosphinothricin acetyltransferase; DsRed, DsRed red fluorescent protein; GFP, green fluorescent protein; TCVCP, Turnip crinkle virus coat protein; HCPro, potyvirus helper component-protease protein.

FIG. 3A shows western blot analysis using an anti-GFP antiserum. Samples of total proteins (15 µg) extracted from soybean plants subjected to the following treatments were used: mock-inoculated (1st trifoliolate; lane 1), wild-type BPMV K-G7-infected (1st trifoliolate; lane 2), pGG7R2-GFP-infected (1st and 2nd trifoliolate leaves; lanes 3 and 4, respectively), and pGHoR2-GFP-infected (1st and 2nd trifoliolate leaves; lanes 5 and 6, respectively). Purified His6-tagged GFP protein (50 ng) was included in lane 7. Lane M contains low molecular weight protein markers. In FIG. 3B, levels of protein loading were assessed by SDS-PAGE analysis and Coomassie blue staining of the proteins tested in FIG. 3A.

FIGS. 4A and 4B show Northern blot hybridization analysis to assess the stability of foreign gene inserts. RNA extracted from purified virions from soybean plants previously inoculated with the following virus isolates or transcripts were used: 1, wild-type strain K-Ho1; 2, wild-type strain K-G7; 3, pGHoR1+ pGG7R2-GFP transcripts; 4, pGHoR$_1$+pGG7R2-DsRed transcripts; 5, pGHoR1+pGHoR2-GFP transcripts; and 6, pGHoR1+pGHoR2-DsRed transcripts. In FIG. 4A, a probe specific for K-Ho1 RNA2 (type II) was used. In FIG. 4B, a probe specific for K-G7 RNA2 (type I) was used. Note that the recombinant RNA2 constructs containing GFP or DsRed (lanes 3-6) are larger in size than those of the wild-type RNA2 (lanes 1 and 2). In FIG. 4C, levels of RNA loading were assessed by ethidium bromide staining of viral RNA.

FIGS. 7A and 7B show phenotypes of soybean plants 21 days postinoculation with the BPMV vector carrying a fragment of the soybean PDS gene (pGG7R2-PDS) and empty vector control (pGG7R2), respectively. FIGS. 7C-7F show representative 3rd trifoliolate leaves from soybean plants previously inoculated with the pGG7R2-PDS vector showing different degrees of photobleaching are shown. FIG. 7G shows soybean plant previously inoculated with the vector control pGG7R2 showing typical mottling symptoms and no bleaching. FIG. 7H shows mock-inoculated soybean plant. The photographs were taken 21 days postinoculation.

DETAILED DESCRIPTION OF THE INVENTION

Figure 1:
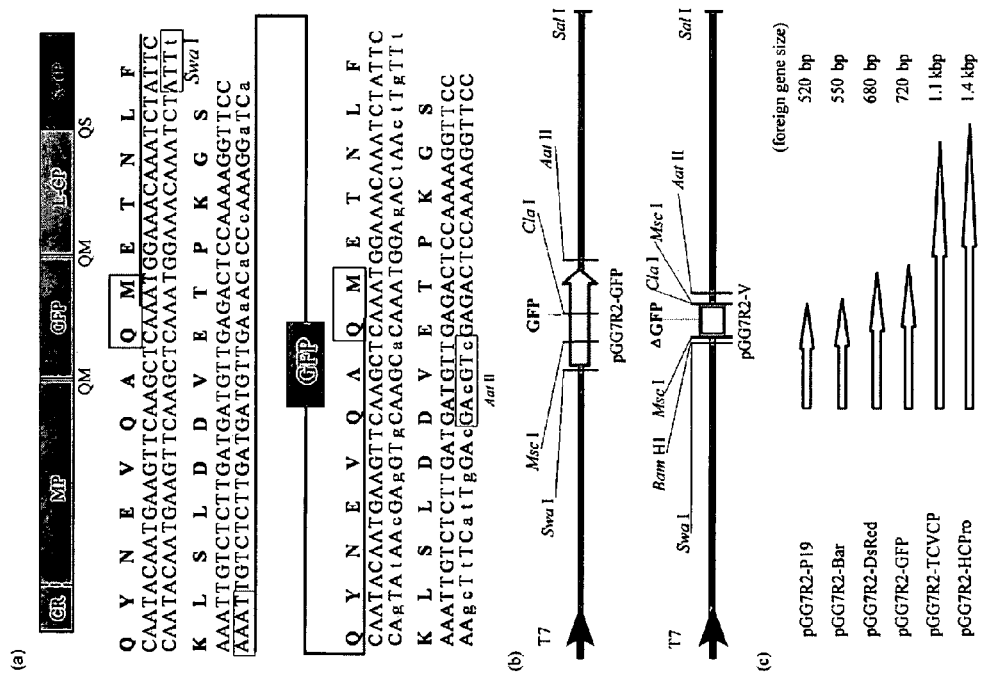
FIGS. 1A-1C shows a schematic representation of BPMV RNA2 vector constructs.

The present invention provides Bean pod mottle virus (BPMV) vectors useful in plants such as soybean. The BPMV vectors of the invention are useful for efficient expression of heterologous proteins in plants such as soybean. The BPMV vectors are also useful for virus-induced gene silencing. The invention also provides methods for expressing a heterologous polypeptide in a plant such as soybean. The present invention provides the first plant-virus-based vector that is appropriate for expression of foreign proteins in soybean. The invention additionally provides methods for virus-induced gene silencing, particularly in a soybean plant, which can be used to determine the function of a gene of interest. The BPMV vectors of the invention advantageously allow efficient systemic expression of foreign polypeptides and nucleic acids in soybean.

BPMV is a member of the genus Comovirus in the family Comoviridae (Lomonossoff and Ghabrial, *Encyclopedia of Plant Pathology*, Vol. 1 (2001)). BPMV has a bipartite positive-strand RNA genome consisting of RNA1 (approximately 6.0 kb) and RNA2 (approximately 3.6 kb) that are separately encapsidated in isometric particles 28 nm in diameter. Two distinct subgroups of BPMV strains, designated subgroups I and II, have been previously isolated and extensively characterized (Gu et al., *Phytopathology* 92:446-452 (2002); Gu et al., *Virology* 333:271-283 (2005)). The BPMV genome is expressed via the synthesis and subsequent proteolytic processing of polyprotein precursors. BPMV RNA-1 codes for five mature proteins required for replication, whereas RNA-2 codes for a putative cell-to-cell movement protein (MP) and the two coat proteins (L-CP and SCP). As disclosed herein, stable BPMV-based vectors can be generated by inserting the gene of interest into the RNA2-encoded polyprotein open reading frame, between the MP and L-CP coding regions, and constructing additional proteinase cleavage sites to flank the foreign protein.

Plant virus-based vectors provide valuable tools for expression of foreign proteins in plants and for gene function studies. None of the previously available virus vectors is suitable for use in soybean. As disclosed herein, Bean pod mottle virus (BPMV)-based vectors are useful for gene expression and virus-induced gene silencing (VIGS) in plants such as soybean. The genes of interest were inserted into the RNA2-encoded polyprotein open reading frame between the movement protein (MP) and the large coat protein (L-CP) coding regions. Additional proteinase cleavage sites were created to flank the foreign protein by duplicating the MP/L-CP cleavage site. To minimize the chances of homologous recombination and thus insert instability, the nucleotide sequence of the duplicated regions was altered without affecting amino acid sequences. The recombinant BPMV constructs were stable following several serial passages in soybean and relatively high levels of protein expression were attained. Successful expression of several proteins with different biological activities was demonstrated from the BPMV vector. These included the reporter proteins GFP and DsRed, phosphinothricin acetyltransferase (encoded by the herbicide resistance bar gene), and the RNA silencing suppressors encoded by Tomato bushy stunt virus, Turnip crinkle virus, Tobacco etch virus, and Soybean mosaic virus. The possible use of BPMV as a VIGS vector to study gene function in soybean was also demonstrated with the phytoene desaturase gene. The results disclosed herein indicate that the BPMV-based vectors are suitable for expression of foreign proteins in soybean and for functional genomics applications.

In one embodiment, the invention provides a Bean pod mottle virus (BPMV) vector containing a nucleic acid sequence encoding an RNA2 polyprotein open reading frame (ORF), wherein the RNA2 polyprotein ORF comprises a first and second protease cleavage site such as a QM cleavage site, wherein the nucleic acid sequences encoding the first and second protease cleavage site such as a QM cleavage sites differ sufficiently to reduce homologous recombination between the QM cleavage site encoding nucleic acid sequences. The protease cleavage site such as a QM cleavage sites can be located, for example, between the movement protein (MP) and large coat protein (L-CP) encoded by the RNA2 polyprotein. The vector can contain restriction sites for insertion of a heterologous sequence between the QM cleavage sites.

As used herein, a "Bean pod mottle virus vector" or "BPMV vector" refers to a nucleic acid vector that, on its own or in combination with other nucleic acids, is capable of generating BPMV when expressed in a host cell or organism. A BPMV vector can be, for example, a BPMV genome such as a genome contained in a whole virus. In addition, a BPMV vector can be a plasmid encoding a portion of a BPMV genome. For example, as disclosed herein, a plasmid encoding one of the two RNAs that comprise the BPMV genome can be used as a BPMV vector that, when combined with a second plasmid that contains the other RNA, results in the production of BPMV virus (see Examples).

As used herein, an "RNA2 polyprotein" refers to the open reading frame encoded by an approximately 3.6 kb RNA, designated RNA2, found in BPMV, as previously described (see Gu et al.,. *Phytopathology* 92:446-452 (2002); Gu and Ghabrial, *Virology* 333:271-283 (2005)). A schematic representation of the genome organization of BPMV RNA2 is shown in FIG. 1A.

As used herein, a "protease cleavage site" refers to an amino acid sequence recognized and cleaved by a site-specific protease, for example, a virally-encoded site-specific protease. Site-specific proteases are well known in the art. In the case where an expression vector such as a BPMV vector of the invention is to be used in a host plant such as soybean, it is understood that the site-specific protease cleavage sites should be recognized by a site-specific protease, for example, a site-specific protease encoded by BPMV RNA1, as disclosed herein. For example, in BPMV, the two RNA viral genomes express polyprotein precursors, which are processed post-translationally to produce mature proteins. Thus, appropriate proteases are expressed that allow proper processing of the polyprotein to mature proteins. An example of such a protease cleavage site is the site between the movement protein (MP) and large coat protein (L-CP) of the RNA2 polyprotein (see FIG. 1). Such a site is cleaved at GlnMet between MP and L-CP and is exemplary of a "QM cleavage site."

As used herein, a "QM cleavage site" refers to a protease cleavage site containing GlnMet. An example of such a cleavage site is the GlnMet sequence that is the cleavage site between the movement protein (MP) and large coat protein (L-CP) of the BPMV RNA2 polyprotein (see FIG. 1A). A QM cleavage site can include additional flanking sequences, for example, from MP and L-CP, to increase efficient cleavage of the QM cleavage site. In a particular embodiment disclosed herein, the 8 C-terminal amino acids of the MP and the 19 N-terminal amino acids of L-CP can be included to increase efficient processing and cleavage of the QM cleavage site. Thus, a QM cleavage site can be a naturally occurring or artificial site engineered to generate a site-specific protease cleavage site, for example, a QM cleavage site flanked by 8 amino acids derived from the C-terminus of the MP and 19 amino acids derived from the N-terminus of the L-CP (see FIG. 1A).

In a particular embodiment, a QM cleavage site can contain the amino acid sequence QYNEVQAQMETNLFKLSLD-DVETPKGS (SEQ ID NO:1). Although exemplified with this particular sequence, it is understood by those skilled in the art that shorter or longer flanking sequences can be used, or even modifications of these sequences, so long as a sufficient cleavage efficiency is achieved suitable for a particular application of the BPMV vectors of the invention. One skilled in the art can readily determine a sufficient cleavage efficiency, for example, by determining the efficiency of production of BPMV, which requires sufficient processing and cleavage of the RNA2 polyprotein to propagate virus. Although exemplified herein using a QM cleavage site, it is understood by those skilled in the art that the invention can also be practiced using other protease cleavage sites so long as sufficient processing occurs so that BPMV is produced and is capable of propagation.

Although exemplified herein as inserting a nucleic acid encoding a heterologous polypeptide between the movement protein (MP) and large coat protein (L-CP) of BPMV RNA2, it is understood that a heterologous polypeptide can be inserted in other locations on RNA2, for example, between other encoded BPMV proteins, or on RNA1 so long as BPMV is produced and is capable of propagation. For example, a heterologous sequence can be inserted downstream from the small coat protein (S-CP) sequence of RNA2 with the engineering of an appropriate protease cleavage site. BPMV RNA2 is about 3.6 kb, and BPMV RNA1 is about 6 kb. BPMV RNA1 and RNA2 are separately packaged in identical capsids, 28 nm in diameter, and the maximum size that can be packaged in BPMV viral capsids is about 6 kb. Therefore, a heterologous sequence up to about 2.4 kb can be accommodated in a viral capsid encapsidating BPMV RNA2, although the efficiency of expression of larger sequences may be reduced. It is also possible to express more than one heterologous sequence, again with appropriate protease sequences engineered. Two heterologous sequences can either be inserted at the same location, for example both between the MP and the L-CP, or one heterologous sequence can be located between the MP and the L-CP and the other after the S-CP, with appropriately engineered protease cleavage sites. If more than one heterologous sequence is included in BPMV RNA2, together the total size of all heterologous sequences included in a single BPMV RNA2 construct should not exceed about 2.4 kb in size since this would exceed the capacity of the viral capsid. Alternatively, a second or additional heterologous sequence can be expressed on a separate RNA2 vector, and first and second RNA2 vectors, each expressing at least one different heterologous sequence, can be co-infected so that more than one heterologous sequence is expressed. If the same protease cleavage site is engineered to effect cleavage of more than one heterologous sequence, the nucleic acid sequence encoding the protease cleavage site(s) can be modified to minimize homologous recombination, as disclosed herein.

In addition to using a BPMV RNA2 vector, it is possible that a BPMV RNA1 based vector could be used to express a heterologous sequence by appropriate engineering of restriction sites for insertion of heterologous sequences, as described for RNA2. RNA1 contains the coding regions of five proteins: from the 5'-nd proteaase-cofactor (Co-pro), helicase (Hel), VPg, protease (Pro) and RNA-dependent RNA polymerase (RdRp). The intermediate polyproteins Hel+VPg and Pro+RdRp play important roles in replication. The cleavage site between Co-pro and Hel, which is glutamine:alanine (QA), is an exemplary site for inserting a heterologous sequence. However, since the RNA1 vector is about 6 kb and the capsid size limit is about 6 kb, it is likely that only small heterologous sequences can be accommodated in an RNA1-based vector. One skilled in the art can readily determine appropriate protease cleavage sites, cloning sites and sizes of heterologous sequences suitable for expression from an RNA1 -based vector by making such constructs and inoculating an appropriate plant host such as soybean and testing for efficient BPMV infection. An RNA1 -based vector with an inappropriate insert of a heterologous sequence can be readily determined since such a vector would result in poor if any BPMV production and, conversely, an appropriate insert of a heterologous sequence can be determined based on sufficient BPMV production.

As used herein, the phrase "differ sufficiently to reduce homologous recombination," refers to a difference in homology between two nucleic acid sequences such that the amount of homologous recombination between the sequences is reduced. For example, in an embodiment of the invention in which a protease cleavage site such as a QM cleavage site is present as two copies, the nucleic acid sequences encoding the protease cleavage sites can be similar or identical if the protease cleavage sites are similar or identical. In such a case, the homology between the nucleic acid sequences encoding the protease cleavage site can undergo homologous recombination. In the case where a nucleic acid encoding a heterologous polypeptide is inserted between the protease cleavage sites, homologous recombination would result in loss of the heterologous sequence and therefore decreased expression of the heterologous polypeptide. To minimize the chance of recombination, the nucleic acid sequences encoding the two copies of the protease cleavage site can be modified based on the degeneracy of the genetic code such that the same amino acids are encoded. For example, FIG. 1 shows a particular embodiment in which the third nucleotide of each codon is changed in one copy of a QM cleavage site so that the encoded amino acids remain the same. Although exemplified with one of the nucleic acid sequences encoding one of the protease cleavage sites being modified, it is understood that one or both sequences can be modified so long as there is a sufficient difference in homology to reduce homologous recombination between the sequences. For example, instead of modifying one copy, it is possible to modify both nucleic acids, for example, by alternating modified codons in the two copies, which would similarly result in reduced homology between the two sequences and therefore reduce homologous recombination. One skilled in the art can readily determine a difference in homology sufficient to reduce homologous recombination, for example, by using vectors of the invention, inoculating a suitable host plant such as soybean and determining the amount of homologous recombination that has occurred. If homologous recombination has occurred at a level that makes a particular BPMV vector unsuitable for a particular use, one skilled in the art can make further changes in homologous sequences in order to reduce the amount of recombination that occurs. Furthermore, although FIG. 1 shows particular changes in codons, it is understood that one skilled in the art can choose other codons that encode the same amino acid, if desired.

Thus, in a particular embodiment, the invention provides a vector in which each codon encoding the QM cleavage site differs between the nucleic acid sequences encoding the first QM cleavage site and the second QM cleavage site. In one embodiment, one of the QM cleavage sites can comprise the amino acid sequence QYNEVQAQMETNLFKLSLDDVETPKGS (SEQ ID NO:1). In another embodiment, the amino acid sequences of the first and second QM cleavage sites are identical, and can be, for example, the amino acid sequence QYNEVQAQMETNLFKLSLDDVETPKGS (SEQ ID NO:1). In still another embodiment, the vector can contain a nucleic acid sequence encoding a heterologous polypeptide inserted between the first and second QM cleavage sites, for example, between BCMV movement protein (MP) and large coat protein (L-CP).

As disclosed herein and exemplified in FIG. 1, a BPMV vector can be modified to include cloning sites for convenience of introducing a heterologous nucleic acid into the vector. It is understood that suitable restriction sites, including those disclosed herein and shown in FIG. 1 as well as other restriction sites, can be included in a BPMV vector of the invention, as desired.

As used herein, the term "heterologous," when used in reference to a polypeptide, nucleic acid or gene, refers to a polypeptide, nucleic acid or gene that is not naturally expressed, for example, by a BPMV or host organism. In reference to a BPMV vector, heterologous refers to a polypeptide, nucleic acid or gene that is not naturally expressed by a BPMV.

The invention also provides a method for expressing a heterologous polypeptide in a plant such as a soybean plant. The method can include the step of inoculating a soybean plant with Bean pod mottle virus (BPMV) RNA1 and recombinant RNA2, wherein the recombinant BPMV RNA2 comprises a nucleic acid sequence encoding an RNA2 polyprotein open reading frame (ORF), wherein the RNA2 polyprotein ORF comprises a first and second protease cleavage site such as a QM cleavage site, wherein the nucleic acid sequences encoding the first and second protease cleavage site such as a QM cleavage site differ sufficiently to reduce homologous recombination between the protease cleavage site, such as a QM cleavage site, encoding nucleic acid sequences and wherein a nucleic acid sequence encoding a heterologous polypeptide is inserted between the first and second protease cleavage sites such as QM cleavage sites. In a particular embodiment, the method can be performed with a vector in which the first QM cleavage sites are located between the movement protein (MP) and large coat protein (L-CP) encoded by the RNA2 polyprotein. The recombinant RNA2 can contain restriction sites for inserting the nucleic acid sequence encoding the heterologous polypeptide between the first and second QM cleavage sites. Other BPMV vectors, as disclosed herein, can also be used in a method for expressing a heterologous polypeptide in a plant such as soybean. Such a method can be used, for example, to produce large quantities of a polypeptide of interest. Production of such heterologous polypeptides can be used to produce large quantities of proteins at relatively low cost, for example, to produce a therapeutic polypeptide. A polypeptide can be purified from the plant and used for therapeutic or other purposes. In addition, expression of a heterologous polypeptide such as an antigen can provide a plant or plant-derived product containing the antigen, which can provide a potential low cost oral vaccine containing an appropriate antigen.

Another important application of plant viral vector systems is in studies on host gene function. With more plant genomic information available, a high throughput tool is required. Virus-induced gene silencing (VIGS) is an exceptional reverse genetics tool that can be employed to generate mutant phenotypes for conveying function to unknown genes. VIGS has many advantages over other methods, for example, it is quick and does not require plant transformation (Burch-Smith et al., 2004). In VIGS systems, viruses are designed to carry partial sequence of known or candidate genes in order to link their function to the mutant phenotype. Replication of the recombinant virus and generation of dsRNA intermediates trigger the RNA-mediated host defense system, resulting in degradation of RNA with sequence identity to the recombinant virus including mRNA of the gene of interest. The targets of VIGS can be a single gene, several members of a gene family, or several distinct genes (Lu et al., *EMBO J.* 22, 5690-5699 (2003a); Peele, et al., *Plant J.* 27:357-366 (2001); Turnage, et al.,. *Plant J.* 30:107- 117 (2002)). Many model host plants including *N. benthamiana*, tomato, tobacco, *Arabidopsis*, and cassava have been explored (Burch-Smith, et al., *Plant J.* 39:734- 746 (2004)). With the current abundance of genomic information on soybean and model legume species (Stacey, et al., *Plant Physiol.* 135:59-70 (2004)), it is timely to apply VIGS to soybean to enhance knowledge of gene function in such a major legume crop. As disclosed herein, BPMV vectors of the invention can be used as a VIGS vector for studies on gene function in soybean.

The invention additionally provides a method for virus-induced gene silencing in a soybean plant and vectors useful in a method for virus-induced gene silencing. Such a method can include the step of inoculating a soybean plant with Bean pod mottle virus (BPMV) RNA, wherein the BPMV RNA comprises a nucleic acid sequence encoding at least a portion of a gene endogenous to the soybean plant. For virus-induced gene silencing, a partial or entire sequence of an endogenous gene can also be located in the untranslated regions (UTRs) of RNA2, or in RNA1 if the sequence is small enough to be accommodated, as discussed above, since it is the expression of the nucleic acid encoding at least a portion of an endogenous gene that results in gene silencing. For a virus-induced gene silencing vector, the insertion in the UTRs can be facilitated by engineering appropriate restriction sites for insertion of the endogenous gene, so long as the inserted endogenous sequence does not impair viral RNA replication and a sufficient amount of infective BPMV is produced.

As used herein, the term "endogenous," when used in reference to a polypeptide, nucleic acid or gene, refers to a polypeptide, nucleic acid or gene that is expressed by a host. For example, using a BPMV vector of the invention for a method of virus-induced gene silencing, a BPMV vector is engineered to express at least a portion of a gene endogenous to the host plant such as soybean. In such a case, the endogenous gene is already expressed in the host plant.

In one embodiment, the method for viral-induced gene silencing can be performed with a vector containing a nucleic acid sequence encoding at least a portion of an endogenous gene that is encoded by an RNA2 polyprotein open reading frame (ORF). In another embodiment, RNA2 polyprotein ORF can comprise a first and second protease cleavage site such as a QM cleavage site, wherein the nucleic acid sequences encoding the first and second protease cleavage sites such as QM cleavage sites differ sufficiently to reduce homologous recombination between the protease cleavage site encoding nucleic acid sequences and wherein the nucleic acid sequence encoding at least a portion of an endogenous gene is inserted between the first and second protease cleavage sites such as QM cleavage sites, for example, between the movement protein (MP) and large coat protein (L-CP) encoded by the RNA2 polyprotein. Other vectors of the invention as disclosed herein can also be used in a method for virus-induced gene silencing.

The results disclosed herein represent the first report to demonstrate that BPMV-based vectors are suitable for efficient expression of heterologous proteins in soybean. The BPMV-RNA2 vector disclosed herein is the first plant-virus-based vector described to date that is appropriate for expression of foreign proteins in soybean. Although the CPMV-RNA2 vector (Gopinath et al., *Virology* 267:159-173 (2000)) could potentially be used as an expression vector in soybean, it is unstable, and CPMV infection induces severe symptoms on soybean (Anjos et al., *Phytopathology* 82:1022-1027 (1992)). Furthermore, soybean is not a natural host for CPMV, and the virus is not believed to be present in the United States (Lomonossoff, *Encyclopedia of Virology*, 2nd ed pp. 285-291 (1999)). Thus, CPMV-based vectors cannot be released in the field in the U.S. or other countries where CPMV is not endemic for practical applications. The instability of the CPMV-RNA2 vector appears to be related to homologous recombination, which may occur as a consequence of duplication of the cleavage sites that border the inserted foreign protein. In engineering the BPMV-RNA2 vector disclosed herein, the nucleotide sequence of the duplicated regions were altered based on degeneracy of the genetic code without affecting amino acid sequence in order to minimize the chances of homologous recombination.

The level of foreign gene expression, as exemplified by the BPMV-GFP vector, was estimated to account for 1% of total soluble proteins (see Example III). This level is comparable to that reported for the PVX-based vectors (Culver, *Virology* 226:228-235 (1996)).

Soybean is the top oilseed crop in the world and provides an extremely valuable, multi-billion dollar, source of high quality protein. It is highly desirable to increase the level of soybean resistance to environmental stress, targeted pests, and diseases in commercial varieties. The availability of the BPMV expression vector allows rapid evaluation of candidate proteins with antifungal or insecticidal activities as well as other valuable proteins that may enhance the commercial value of soybean. The potential advantages that make BPMV an attractive vector system are that the virus (including mild strains) multiplies to high levels in soybean (20-50 mg virus from 100 g leaf tissue) and that it is stable and easily purified. For inoculation purposes under greenhouse conditions, purified recombinant BPMV virions or extracts from fresh or dried leaves from plants previously infected with the recombinant vector were successfully used. Although agroinoculation via leaf infiltration is known to provide the most efficient means for introducing cDNA-derived viral RNA into the leaves of some plant species (Lu et al., *Methods* 30:296-303 (2003b)), soybean leaves are difficult to infiltrate, and no alternative conventional methods are presently available for soybean agroinoculation.

The BPMV-based vector is suitable for use as a VIGS vector to study gene function in soybean. The bleached silencing phenotype of soybean plants inoculated with BPMV vector carrying a fragment of the soybean PDS gene was stable over time as it continued to develop throughout the duration of the experiment (35 dpi)(see Example VI). VIGS has proved to provide an impressive means to study gene function and has also been demonstrated to be particularly useful in plants with genetic redundancy like soybean (Lawrence et al., *Plant J.* 36:114-121 (2003)). The most widely used VIGS vectors are based on potato virus X (PVX) or tobacco rattle virus (TRV) (Liu et al., *Plant J.* 31 :777-786 (2002); Lu et al., *EMBO J.* 22:5690-5699 (2003a)), and their applications have been mainly studied in *N. benthamiana*, where VIGS response is generally stronger and more enduring than in other plants (Lu et al., supra, 2003a). Recently, efficient VIGS systems have also been developed for a few additional host plants including barley, tomato, and *Pisum sativum* (Constantin et al., *Plant J.* 40:622-631 (2004); Holzberg et al., *Plant J.* 30:1-13 (2002); Liu et al., *Plant J.* 31:777-786 (2002)). There is presently an urgent need for a VIGS vector suitable for use in soybean considering the substantial wealth of available information on soybean genomics. None of the previously established VIGS vectors is appropriate for use in soybean. Although full-length cDNA infectious clones are available for the potyviruses SMV and Clover yellow vein virus that can infect soybean (Hajimorad et al., *Virology* 314:497-509 (2003); Masuta et al., *Plant J.* 23:539-546 (2000)), neither has been evaluated as a VIGS vector. Potyviruses are unlikely to provide efficient VIGS vectors because they encode potent suppressors of RNA silencing (HC-Pro proteins). HC-Pro has been shown to suppress both VIGS and transgene-induced RNA silencing (Anandalakshmi et al., *Proc. Natl. Acad. Sci. U.S.A.* 95:13079-13084 (1998); Roth et al., *Virus Res.* 102:97-108 (2004)).

The results disclosed herein with the recombinant BPMV-PDS indicate that the BPMV-based VIGS vector induced efficient and reliable gene silencing in soybean (see Example VI). This represents the first report providing experimental evidence that the RNA silencing machinery is operational in soybean. RNA silencing (also known as posttranscriptional gene silencing or PTGS) is implicated in the synergistic interaction between BPMV and SMV in dually infected soybean plants that results in enhanced symptom severity and accumulation of BPMV (Anjos et al., *Phytopathology* 82:1022-1027 (1992)). This synergy is caused by SMV HC-Pro-mediated suppression of RNA silencing, as was clearly demonstrated by inoculation of soybean with the recombinant BPMV-HC-Pro construct, as disclosed herein. BPMV does not appear to code for any suppressors of RNA silencing. In a recent study, using an *Agrobacterium*-mediated transient expression system, suppression of GFP-RNA silencing in transgenic *N. benthamiana* infiltrated with any of the recombinant agrobacteria carrying BPMV coding regions for the primary or secondary polyprotein precursors or for any of the individual mature proteins was demonstrated (Gu and Ghabrial, supra, 2005). In apparent contrast, the small coat protein (S-CP) of the related CPMV was reported to function as a weak suppressor of amplicon-induced silencing in *N. benthamiana* (Liu et al., supra, 2004). Similar experiments cannot be carried out with BPMV because it does not infect *N. benthamiana*. Assuming that BPMV S-CP, like that of CPMV, functions as a weak suppressor of RNA silencing, such activity has little or no effect on the RNA silencing system of soybean, as judged by the results of the BPMV-PDS experiments. Therefore, in a method for viral-induced gene silencing, RNA silencing suppressors can optionally be included, as discussed above and described in Example VI. The inclusion of RNA silencing suppressors can enhance the gene silencing and effects seen from the gene silencing.

There are presently available more than 300,000 expressed sequence tags (ESTs) that are derived from over 80 different cDNA libraries representing a wide range of soybean organs, developmental stages, genotypes, and environmental conditions (Stacey et al., *Plant Physiol.* 135:59-70 (2004)). This soybean EST collection provides a large resource of publicly available genes and gene sequences that can potentially provide valuable insight into structure and function of this model crop legume. VIGS presents an ideal tool for large-scale functional genomics to convert the soybean sequence information into functional information. The results disclosed herein indicate that the BPMV-based vector is suited for this purpose. A possible disadvantage of VIGS is that symptoms induced by virus infection may obscure the phenotype associated with silencing of the gene of interest. This should not be a problem with the BPMV-soybean system based on current knowledge of symptom severity determinants in BPMV. BPMV-induced symptom severity has recently been mapped to RNA1 and more specifically to the coding regions of the protease cofactor and the C-terminal half of the putative helicase. Furthermore, the amino acid positions that are responsible for differences in symptom severity between mild and severe strains were identified (Gu et al., *Virology* 333:271-283 (2005)). Since BPMV RNA2 does not play a direct role in symptom severity and since it is the genomic segment that carries the foreign gene of interest, it is then a simple matter to avoid interference from virus symptoms by using RNA1 derived from a mild strain (as demonstrated with the mild strain K-Ha1) or from a modified RNA1 engineered to cause attenuated symptoms combined with enhanced production of the recombinant RNA2.

Although exemplified herein with soybean, it is understood that a BPMV vector of the inventions can be used in other suitable host plant organisms that support the propagation of BPMV. For example, other cultivars of bean and leguminous weeds are also known to be hosts for BPMV (Geisler et al., *Plant Dis.* 86:1280-1289 (2002)). Therefore, the vectors of the invention can be used in methods in other suitable host plants as with soybean.

It is understood that modifications which do not substantially affect the activity the various embodiments of this invention are also provided within the definition of the invention provided herein. Accordingly, the following examples are intended to illustrate but not limit the present invention.

EXAMPLE I

Methods for Generation and Analysis of BPMV Vectors

Virus strains. BPMV strains KY-Hopkins 1 (K-Ho1), KY-Hancock 1 (K-Ha1), and KY-Graves 7 (K-G7) have been previously described, and their complete nucleotides sequences have been reported (Gu et al., *Phytopathology* 92:446-452 (2002); Gu and Ghabrial, *Virology* 333:271-283 (2005), each of which is incorporated herein by reference). The nucleotide sequences are available at GenBank: K-G7, accession No. U70866 (version dated Mar. 16, 2001, which is incorporated herein by referenc) and accession No. M62738 (version dated Apr. 28, 1993, which is incorporated herein by reference); K-Ha1, RNA1, accession No. AF394606 (version dated Feb. 25, 2005, which is incorporated herein by reference), RNA2, accession No. AF394607 (version dated Feb. 25, 2005, which is incorporated herein by reference); K-Ho1, RNA1, accession No. AF394608 (version dated Feb. 25, 2005, which is incorporated herein by reference), RNA2, accession No. AF394609 (version dated Feb. 25, 2005, which is incorporated herein by reference). The BPMV strains were propagated in the soybean cultivar "Essex", and infected tissues were used for virion purification as previously described (Ghabrial et al., *Plant Dis. Rep.* 61:690-694 (1977)). Soybean mosaic virus (SMV) strains G6 and G7 were used for amplification of the HC-Pro coding regions. SMV strain designation was based on the differential reactions of soybean cultivars carrying resistance genes to SMV (Cho and Goodman, *Phytopathology* 69:467-470 (1979); Gunduz et al., *Phytopathology* 94:687-692 (2004)).

RNA extraction and Northern hybridization analysis. Viral RNA was isolated from purified virions by the sodium dodecyl sulfate (SDS)-phenol method (Peden and Symons, *Virology* 155:487-492 (1973)). Total RNA was extracted from plant tissue using a hot phenol method (Verwoerd et al., *Nucleic Acids Res.* 17:2362 (1989)). For Northern blot hybridization analysis, the RNA samples were denatured in the presence of glyoxal and dimethyl sulfoxide and separated by electrophoresis on a 0.8% agarose gel in 10 mM sodium phosphate buffer, pH 6.3 (Sambrook and Russell, *Molecular Cloning: A Laboratory Manual*, 3rd ed. Cold Spring Harbor Laboratory Press, New York (2001)). RNA was transferred onto Hybond-N+ membranes, (Amersham, Piscataway, N.J.), a positively charged nylon membrane with a binding capacity for nucleic acids, according to the manufacturer's instructions. The membranes were then prehybridized, hybridized, and air-dried as previously described (Gu et al., supra, 2002). Full-length RNA1 and RNA2 cDNA clones of strain K-G7 (strain subgroup I) or K-Ha1 (strain subgroup II) were used as templates for probe preparation by the REDIPRIME II random prime labeling system (Amersham), a DNA labeling system, according to the manufacturer's instructions. The Northern blots were exposed to a phosphorimager screen, and the images were visualized with a PHOSPHORIMAGER 445 SI system and analyzed with the IMAGEQUANT 4.1 software program (Amersham).

Construction of BPMV RNA2 vectors. Full-length infectious BPMV RNA2 cDNA clones (pGG7R2 and pGHoR2), derived from subgroup I and II strains, respectively, were used for construction of the BPMV RNA2 vectors. Unless otherwise specified, transcripts derived from plasmid pGHoR1 containing a full-length infectious RNA1 cDNA (type I, RNA1) were used along with transcripts from recombinant plasmids derived from pGG7R2 or pGHoR2 in all inoculations. Plasmids pGHoR1, pGG7R2, and pGHoR2 were described previously (Gu and Ghabrial, supra, 2005).

GFP constructs. The 5'-half of BPMV RNA2 cDNA in plasmids pGG7R2 or pGHoR2 (1830 bp) was amplified by PCR using the primer pair F1 and SwaI-Rev-R2 (Table 1), and the PCR products were cloned into the pGEM-T easy vector (Promega, Madison, Wis.). The resultant clones were digested with SwaI and NcoI, and two clones, pGG7R2-1 and pGHoR2-1, were selected following verification by restriction enzyme digestion and nucleotide sequencing. Clones pGG7R2-1 and pGHoR2-1 were digested with AatII, blunt-ended, and self-ligated to remove the AatII restriction site in the vector and to create the new constructs pGG7R2-2 and pGHoR2-2. The GFP5 gene was amplified using plasmid pZGFP (Soldevila and Ghabrial, *J. Virol.* 74:997-1003 (2000)) as a template and the primer pair GFP-For and GFP-Rev (Table 1). The PCR product was cloned into the pGEM-T easy vector, and the resultant clone (pGGFP-1) was verified by sequencing. The pGG7R2-2 and pGHoR2-2 constructs were digested with SwaI and SalI and ligated into similarly digested pGGFP-1 to generate constructs pGG7R2-3 and pGHoR2-3, respectively. The 3'-half of BPMV RNA2 cDNA in plasmids pGG7R2 or pGHoR2 (1841 bp) was amplified by PCR using the primer pair AatII-For-R2 and R1 (Table 1), and the PCR products were cloned into the pGEM-T easy vector to generate clones pGG7R2-4 and pGHoR2-4, which were verified by sequencing. Clones pGG7R2-4 and pGHoR2-4 were digested with SacI and PstI, blunt-ended, and self-ligated to remove the vector SalI site and to generate clones pGG7R2-5 and pGHoR2-5, respectively. Finally, clones pGG7R2-5 and pGHoR2-5 were digested with AatII and SalI and the resultant smaller fragments were isolated and ligated into AatII/SalIdigested pGG7R2-3 and pGHoR2-3, respectively, to produce the infectious constructs pGG7R2-GFP and pGHoR2-GFP.

TABLE 1

List of primers used to construct BPMV vectors.

| Name | Sequence |
|---|---|
| F1 | TAATACGACTCACTATAGTATTAAAATTTTCATAAGATTTGAAATTTTGATAAACCG (SEQ ID NO: 2) |
| R1 | TTCCGCGGCCGCTATGGCCGACGTCGACTTTTTTTTTTTTTTTT (SEQ ID NO: 3) |
| AatII-For-R2 | GGACGTCGAGACTCCAAAAGGTTCCAT (SEQ ID NO: 4) |
| SwaI-Rev-R2 | AATTTAAATAGATTTGTTTCCATTTGAGC (SEQ ID NO: 5) |
| GFP-For | AATTTAAATTGTCTCTTGATGATGTTGAAACACCCAAAGGATCAATGAGTAAAGGAGAAGAACTTTTCACT (SEQ ID NO: 6) |
| GFP-Rev | GGACGTCGTCCAATGAAAGCTTAAACAAGTTAGTCTCCATTTGTGCTTGCACCTCGTTATATTGTTTGTATAGTTCATCCATGCCATGTG (SEQ ID NO: 7) |
| RFP-For | ATTTAAATTGTCTCTTGATGATGTTGAAACACCCAAAGGATCAATGGCATCCTCTGAAGATGTTATCAAG (SEQ ID NO: 8) |
| RFP-Rev | GACGTCGTCCAATGAAAGCTTAAACAAGTTAGTCTCCATTTGTGCTTGCACCTCGTTATATTGGGCGCCGGTGGAGTGG (SEQ ID NO: 9) |
| VecModi-For1 | AATTTAAATTGTCTCTTGATGATGTTGAAACACCC (SEQ ID NO: 10) |
| VecModi-Rev1 | TTGGCCAGGATCCTTTGGGTGTTTCAACATCATC (SEQ ID NO: 11) |
| VecModi-For2 | ATCGATGGCCACAATATAACGAGGTGCAAGCCCAAATGGAGACC (SEQ ID NO: 12) |
| VecModi-Rev2 | GACGTCGTCCAATGAAAGCTTAAACAAGTTGGTCTCCATTTGGG (SEQ ID NO: 13) |
| SMV-Af | GGATCCTCCCAAAATCCTGAAGCTCAGTT (SEQ ID NO: 14) |
| SMV-Ar | ACTGTCAAAGATCCAAAAGAGTC (SEQ ID NO: 15) |
| SMV-Bf | GACTCTTTTGGATCTTTGACAGT (SEQ ID NO: 16) |
| SMV-Br | TCATCCTCTGTTGCACGATATCACCAACTCT (SEQ ID NO: 17) |
| TEV-P2-For | GGATCCAGCGACAAATCAATCTCTGAGGCA (SEQ ID NO: 18) |
| TEV-P2-Rev | GATATCTCCAACATTGTAAGTTTTCATTTCGGA (SEQ ID NO: 19) |
| TBSV-P19-For | CGCGGATCCATGGAACGAGCTATACAAGGA (SEQ ID NO: 20) |
| TBSV-P19-Rev | TGTGTTGGCCACTCGCTTTCTTTTTCGAAGGT (SEQ ID NO: 21) |
| TCV-CP-For | CGCGGATCCATGGAAAATGATCCTAGAGTC (SEQ ID NO: 22) |
| TCV-CP-Rev | ATTGGATATCAATCCTGAGTGCTTGCCATTTTCC (SEQ ID NO: 23) |
| PDS-For | CCGCGGATCCGCCGCTTGTGGCTATATATCT (SEQ ID NO: 24) |
| PDS-Rev | CACAGATATCTCCTGCACCGGCAATAACGAT (SEQ ID NO: 25) |

DsRed constructs. The DsRed gene was amplified by PCR using plasmid pDsRed2-C1 (Clontech, Palo Alto Calif.), as a template, and primers RFP-For and RFP-Rev (Table 1). The PCR product was cloned into the pGEM-T easy vector to generate clone pGdsRed-1, which was confirmed by sequencing. The DsRed gene was released from pGdsRed-1 by digestion with SwaI and AatII, and the resultant fragment was ligated into plasmids pGG7R2-GFP and pGHoR2-GFP, which were SwaI/AatII-digested, to replace the GFP gene and generate the infectious constructs pGG7R2-DsRed and pGHoR2-DsRed, respectively.

Vector modification. To generate a suitable BPMV-RNA2 vector for cloning and expression of foreign genes, the GFP construct, pGG7R2-GFP (FIG. 1), was modified to remove most of the GFP sequences and to insert two new restriction sites. To introduce a BamHI restriction site into the BPMV RNA2 vector, primers VecModi-For1 and VecModi-Rev1, which partially anneal to each other, were subjected for PCR, and the product was cloned into the pGEM-T easy vector and confirmed by sequencing (pVec-Modi-1). A similar approach was used to introduce a second MscI restriction site into the BPMV RNA2 vector; primers VecModi-For2 and VecModi-Rev2 (Table 1), which partially anneal to each other, were subjected to PCR, and the product was cloned into the pGEM-T easy vector and confirmed by sequencing (pVec-Modi-2). Plasmid pGG7R2-GFP was digested with SwaI and MscI, and the resultant larger fragment was isolated and ligated into similarly digested pVecModi-2 to generate plasmid pGG7R2-6. The latter was then digested with ClaI and AatII, and the resultant larger fragment was isolated and ligated into similarly digested pVecModi-1 to generate the BPMV-RNA2 vector, designated pGG7R2-V (FIG. 1).

Bar constructs. The bar gene (coding for phosphinothricin acetyltransferase) was released from plasmid pBG-GD (Straubinger et al., *Fungal Genet. Newsl.* 39:82-83 (1992)) by digestion with BglII, blunt-ended with Klenow large fragment DNA polymerase (Invitrogen, Carlsbad Calif.), and then digested with BamHI. The DNA fragment containing the bar gene was gel-purified and ligated into pGG7R2-V, previously digested MscI and BamHI, to produce pGG7R2-Bar.

Constructs of RNA silencing suppressors. TBSV P19 gene was amplified from plasmid PZPTBSVp19 (Qu et al., *J. Virol.* 77:511-522 (2003)) using the primer pair TBSV-P19-For and TBSV-P19-Rev (Table 1), and the resulting PCR product was cloned into the pGEM-T easy vector. Clones in the correct orientation were selected and digested with BamHI and MscI, and the released P19 gene was cloned into BamHI/MscI-digested pGG7R2-V to produce pGG7R2-P 19. Turnip crinkle virus (TCV) coat protein (CP) gene was amplified from plasmid PZP-TCVCP (Qu et al., supra, 2003) using primers TCV-CP-For and TCV-CP-Rev (Table 1), and the resultant PCR product was cloned into the pGEM-T easy vector. Clones in the correct orientation were selected and digested with BamHI and EcoRV, and the released CP gene was cloned into BamHI/MscI-digested pGG7R2-V to produce pGG7R2-TCP. The coding region of Tobacco etch virus (TEV) HC-Pro was amplified by PCR using plasmid pTEV7D, which contains a full-length cDNA of TEV-RNA (Dolja et al., *Proc. Natl. Acad. Sci. U.S.A.* 89:10208-10212 (1992)), as a template along with primers TEV-P2-For and TEV-P2-Rev (Table 1). The resultant PCR product was cloned into the pGEM-T easy vector, and clones in the correct orientation were digested with BamHI and EcoRV. The released HC-Pro gene was then cloned into BamHI/MscI-digested pGG7R2-V to produce pGG7R2-HCPro(T). An RT-PCR approach was used to clone SMV HC-Pro coding region. A reverse primer (SMVBr; Table 1) was used for first strand cDNA synthesis with total RNA from soybean leaves infected with SMV strains G6 or G7 and a SUPERSCRIPT II reverse transcription kit (Invitrogen). To eliminate a BamHI site in the SMV-HC-Pro coding region without changing the amino acid sequence, a two-step PCR method was used. In the first step, two overlapping cDNA fragments containing the entire HC-Pro sequence (fragments A and B covering the 5' and 3' halves, respectively) were PCR-amplified in separate reactions using first strand cDNA as a template and two pairs of primers (SMV-Ar and SMV-Af and SMV-Br and SMV-Bf). The reverse primer of fragment A (SMV-Ar; 23 nucleotides in length) is complementary to the forward primer of fragment B (SMV-Bf). Equimolar amounts of each fragment along with primers SMV-Br and SMV-Af were used for the second step PCR. The final PCR product was cloned into the pGEM-T easy vector, and clones in the correct orientations were confirmed by sequencing. The inserted HCPro genes from strains G6 and G7 were digested with BamHI and EcoRV and ligated into BamHI/MscI-digested pGG7R2-V to produce pGG7R2-HCPro(S6) and pGG7R2-HCPro(S7), respectively.

Phytoene desaturase (PDS) constructs. Soybean genomic DNA was extracted from leaves of the soybean cultivar 'Essex,' as previously described (Srinivasa et al., *Phytopathology* 91:831-838 (2001)). A 318 bp PDS fragment was PCR-amplified using the primer pair PDS-sen5-For and PDS-sen5-Rev (Table 1). The PCR product was digested with BamHI and EcoRV and ligated into BamHI/MscI-digested pGG7R2-V to generate construct pGG7R2-PDS.

Nucleotide sequencing. All sequencing was done using the BIGDYE Terminator DNA Sequencing Kit (Applied Biosystems, Foster City Calif. USA) and the ABI Prism 310 genetic analyzer. Sequence analysis was performed using the DNA strider (CEA, France) and Vector NTI programs (Informax Inc., Frederick, Md., USA).

In vitro transcription and inoculation. Plasmids pGHoR1 (containing full-length cDNA clone to type I RNA1, from strain K-Ho1) and pCRHaR1 (containing full-length cDNA to type II RNA1, from strain K-Ha1) were used as templates for in vitro transcription as previously described (Gu and Ghabrial, supra, 2005). After transcription, 5 µl samples of the reaction mixture were analyzed on a 1% agarose gel to assess yield and quality of the transcripts. RNA transcripts (a mixture of RNA1 and RNA2 transcripts) were used to inoculate fully expanded primary soybean leaves by rub inoculation.

Protein expression and Western blot analysis. Total protein extraction from soybean leaves was performed as described by Osherov and May (*Fungal Genet. Newsl.* 45:38-40 (1998)). Protein concentration was estimated by the Bio-Rad protein assay method (Bio-Rad Laboratories, Hercules Calif.). A known amount of purified, bacterially expressed, GFP was used as a standard in assays to assess expression levels of recombinant GFP. For this purpose, the wild-type GFP gene was released from plasmid pIVEX2.3 (Roche Applied Science, Indianapolis, Ind., USA) by digestion with XbaI and BamHI and cloned into pET21d vector (EMD Biosciences, San Diego, Calif., USA). The resulting clone was transformed into *E. coli* strain BL21 (DE3), and GFP expression was induced and purified according to manufacturer's instructions (EMD Biosciences). Western blot analysis was carried out as previously described (Srinivasa et al., supra, 2001) using antisera to BPMV CP and GFP (Chemicon International Inc., Temecula, Calif.). GFP expression level was assessed using IMAGEQUANT v5.2 (Amersham).

Fluorescence detection. Whole leaf green fluorescence images were acquired using BioChemi-V cooler camera mounted on Epi Chemi II Darkroom (UVP company, Upland, Calif., USA). The settings were overhead excitation light 365 nm and filter set as SYBR Green (Hoechst Blue). The Labworks Ver 4.0.0.8. software was used for acquiring images, which were exported as TIFF files.

Herbicide treatment. One-week-old soybean seedlings were inoculated with the recombinant BPMV-bar construct. Two weeks later, the infected soybean plants were sprayed with the herbicide Liberty, which contains glufosinate-ammonium (GA) as the active ingredient (Aventis CropScience, Research Triangle Park, N.C.), at a concentration of 0.1% GA (w/v) in deionized water. The soybean plants were photographed 3 weeks after herbicide treatment.

EXAMPLE II

Construction of BPMV RNA2 Vectors

Figure 2:
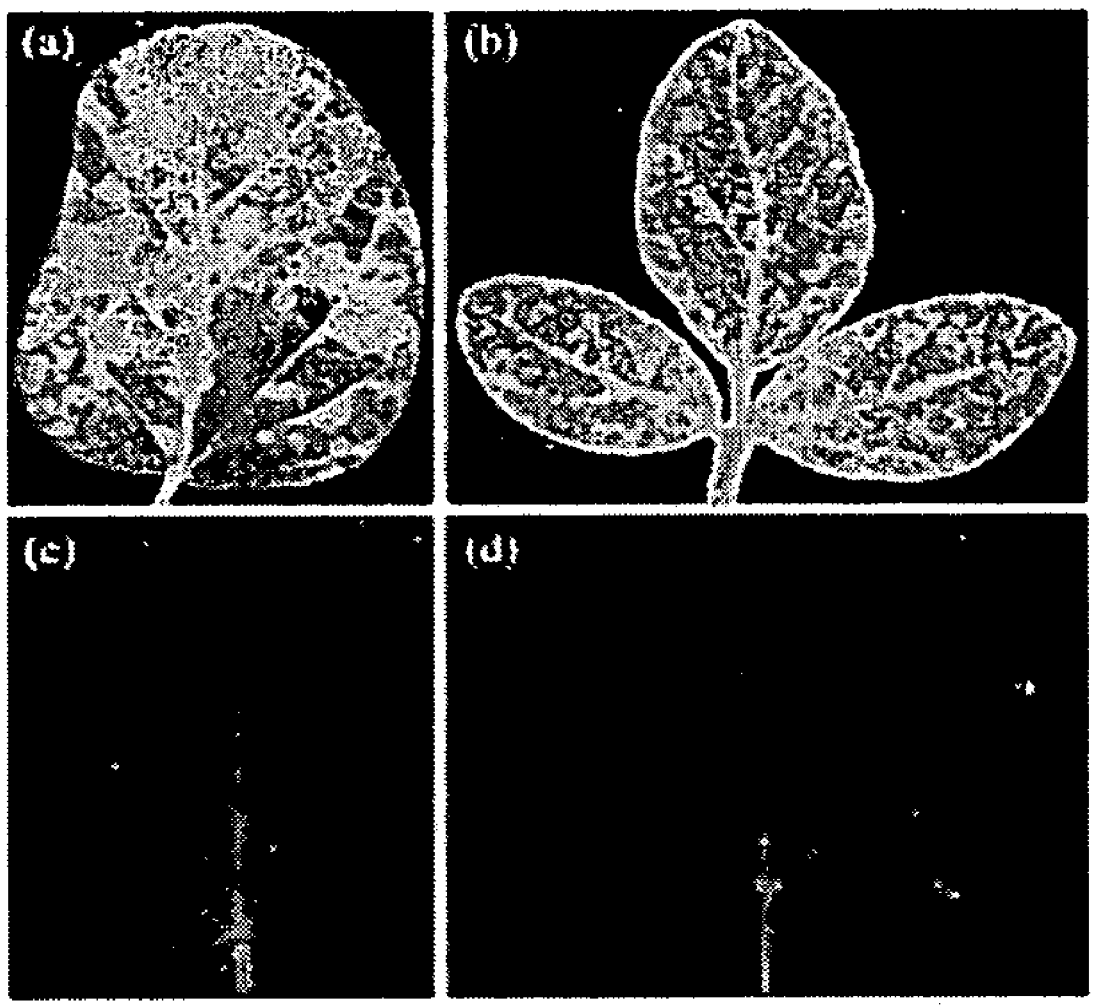
FIGS. 2A-2D shows green fluorescence on inoculated and systemic leaves of soybean plants. Soybean seedlings were inoculated on their primary leaves with leaf extracts prepared from plants infected with the BPMV-GFP construct after four serial passages in soybean. Alternatively, the primary leaves were inoculated with the wild-type K-Ho1 isolate or mock-inoculated with buffer only. The primary leaf (FIG. 2A) and second trifoliolate leaf (FIG. 2B) from a soybean plant, previously inoculated with the BPMV-GFP construct, showed intense green fluorescence under UV light. No fluorescence was detected on the mock-inoculated primary leaf (FIG. 2C) or on the second trifoliolate of K-Ho1-infected plants (FIG. 2D). Leaves in FIGS. 2A, 2B, and 2D showed symptoms typical of isolate K-Ho1; mosaic and necrosis on inoculated leaves and mottling on systemic leaves. All leaves were photographed under UV light 11 days postinoculation.

For development of BPMV as a viral vector for expression of heterologous proteins in soybean, the gene of interest was inserted into the RNA2-encoded polyprotein ORF between the MP and the L-CP coding regions. Additional proteinase cleavage sites were created to flank the foreign protein by duplicating the MP-LCP cleavage site (as exemplified by the GFP gene construct in FIG. 1A). The coding sequences for the 8 C-terminal amino acids of the MP and the 19 N-terminal amino acids of the L-CP were included for efficient processing. To minimize the chances of homologous recombination, thus instability, the third nucleotide in each codon was changed based on codon degeneracy (in accordance with BPMV codon usage) so that the encoded amino acid residues remained unchanged (FIG. 1A). Initially, BPMV recombinant vectors expressing GFP or DsRed were constructed and shown to be infectious and stable. Under greenhouse conditions, the GFP construct was passaged 4 times without any apparent reduction in fluorescence intensity (FIG. 2).

The BPMV vector was further modified to include additional cloning sites (FIG. 1B); foreign genes can be cloned by digesting the vector pGG7R2-V with BamHI and MscI (for directional cloning) or by digestion with MscI (for blunt end cloning). Two sets of BPMV RNA2 vectors corresponding to BPMV RNA2 subgroups I and II were constructed.

Several different genes that varied in size and biological activity were cloned into the BPMV RNA2 vectors utilizing the BamHI and MscI restriction sites in the modified vector (FIG. 1B). In all cases, the foreign protein was placed between two artificial cleavage sites with duplication of 27 virus-derived amino acids, for efficient processing, as described for the GFP constructs. These genes ranged in size from 520 bp to 1400 bp (FIG. 1C) and included the herbicide resistance bar gene (coding for phosphinothricin acetyltransferase) and several viral-encoded suppressors of host-mediated RNA silencing. These included the P-19 and coat protein (CP) encoded by Tomato bushy stunt virus (TBSV) and Turnip crinkle virus (TCV), respectively, and the helper component-protease (HCPro) encoded by Soybean mosaic virus (SMV) and Tobacco etch virus (TEV).

EXAMPLE III

Expression Levels of Foreign Genes from BPMV Vectors

Figure 3:
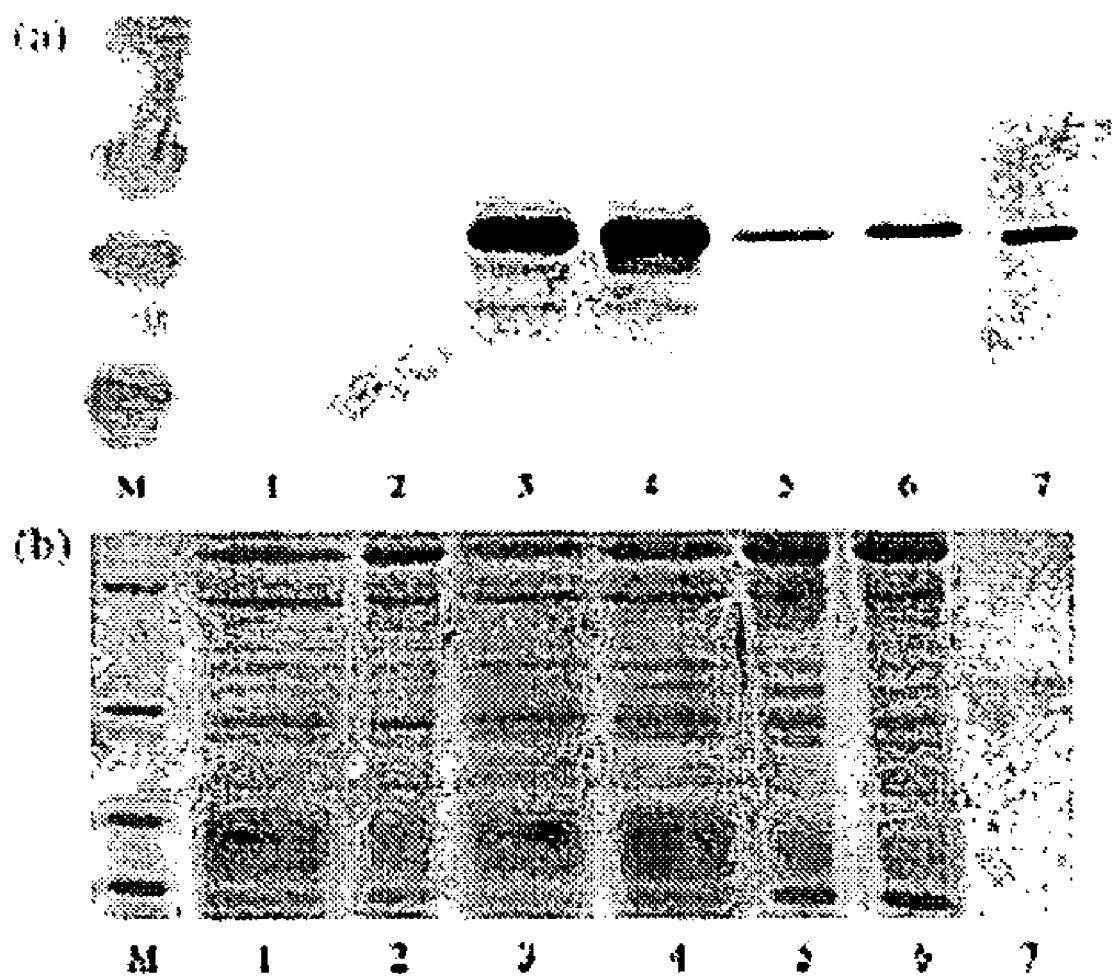
FIGS. 3A-3B shows immunoblot analysis of total proteins from soybean plants infected with GFP constructs.

The recombinant BPMV-GFP constructs were used to evaluate foreign gene expression levels in soybean. The primary leaves of 7- to 10-day-old soybean seedlings were inoculated with the BPMV-GFP constructs derived from either subgroup I or subgroup II BPMV RNA2. Three weeks postinoculation, total soluble proteins were extracted from the first and second trifoliolate leaves and subjected to Western blot analysis (FIG. 3). Affinity-purified His-tagged GFP, which was expressed in *E. coli,* was used as a control (FIG. 3, lane 7). Interestingly, the expression level provided by subgroup I RNA2 vectors was higher than that obtained with subgroup II RNA2 vectors in both the first and second trifoliolate leaves (compare lanes 3 and 5, FIG. 3). To assess the GFP expression level, the Western blot was scanned, and the generated images of band intensity were analyzed by the ImageQuant™ v5.2 program (Amersham). The results indicated that GFP expression level can account for as much as approximately 1% of total proteins in soybean.

EXAMPLE IV

Stability of the Foreign Gene Expressed from BPMV RNA2 Vectors

Figure 4:
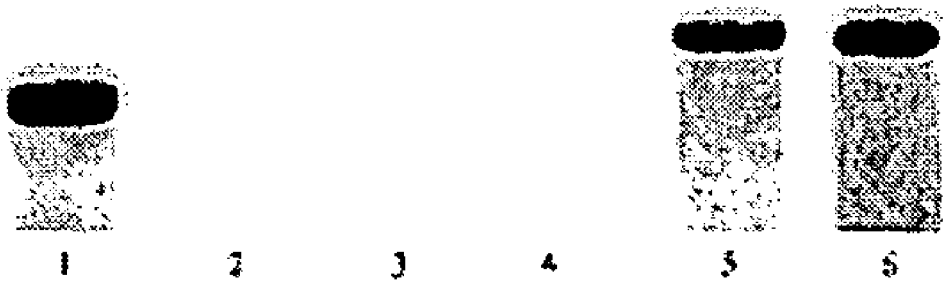
FIGS. 4A-4C shows the stability of the GFP and DsRed genes expressed from the BPMV vectors.
Figure 4:
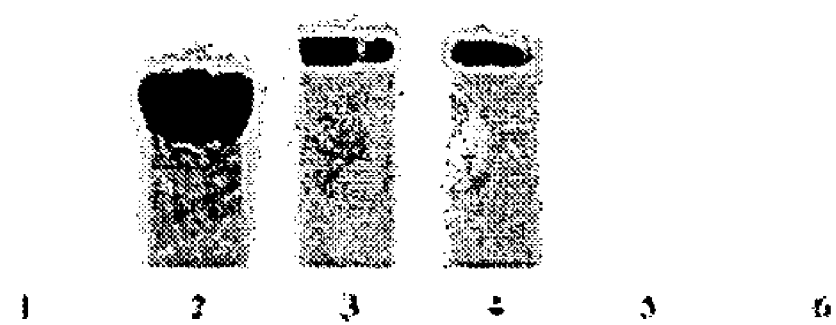
Figure 4:
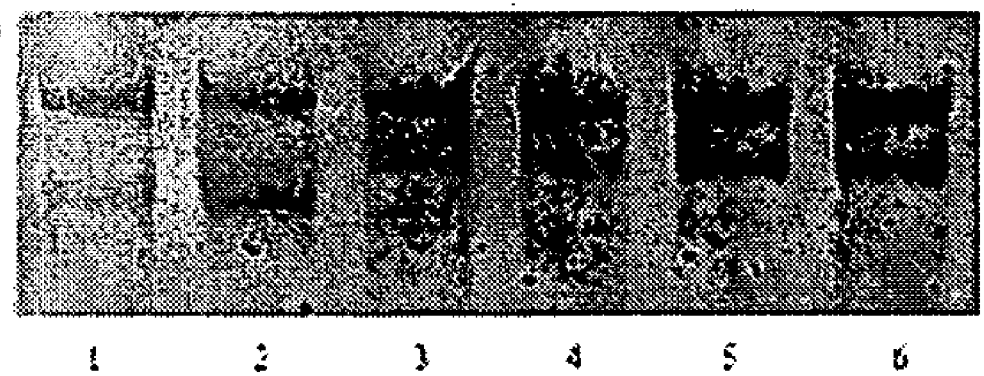

To assess the stability of inserted foreign genes during serial plant passages, virions were purified from soybean plants previously infected with the BPMV-GFP or BPMV-DsRed constructs. Following three passages of the recombinant BPMV vector, viral RNA was isolated from purified virions and subjected to Northern hybridization analysis (FIG. 4). Only a single band of the predicted size of the recombinant RNA2 containing the coding sequences for GFP or DsRed was resolved. No wild-type RNA2 was detected even following extended overexposure of the blots. Furthermore, fluorescence due to expression of GFP or DsRed was readily detected in the seed coats from immature seeds, suggesting that the foreign genes were stably expressed at a later developmental stage during pod formation.

As disclosed herein, the BPMV-GFP vector was stable after four serial passages in soybean, and no traces of wild-type virus were detected by Northern hybridization analysis (FIG. 4). The finding that the bright green fluorescence was maintained throughout the soybean plant including the seed coats of immature seeds provides further evidence for the endured stability of the GFP construct. The BPMV-GFP vector was also stable after three serial passages in *Phaseolus vulgaris* cv. Black Velvet. In addition to soybean and a few cultivars of bean, the host range of BPMV is very limited and includes only some leguminous weeds (Giesler, et al., *Plant Dis.* 86:1280-1289 (2002)). Because BPMV does not infect *N. benthamiana* or tobacco, which are known to support the amplification and foreign gene expression of most established plant viral vectors, it is not possible to compare the BPMV-based vectors with others in regard to insert instability. It is known that host factors affect viral RNA replication and recombination and may thus contribute to reported differences in the frequencies of viral RNA recombination among diverse host species (Ahlquist, et al., *J. Virol.* 77:8181-8186 (2003); Desvoyes, et al., *Virology* 304:434- 442 (2002); Dzianott, et al., *Virology* 318:482-492 (2004)). It is possible that host factors in soybean play a role in the stability of the BPMV-based vectors by suppressing viral RNA recombination.

EXAMPLE V

Biological Activity of Gene Products Expressed from BPMV RNA2 Vectors

Figure 5:
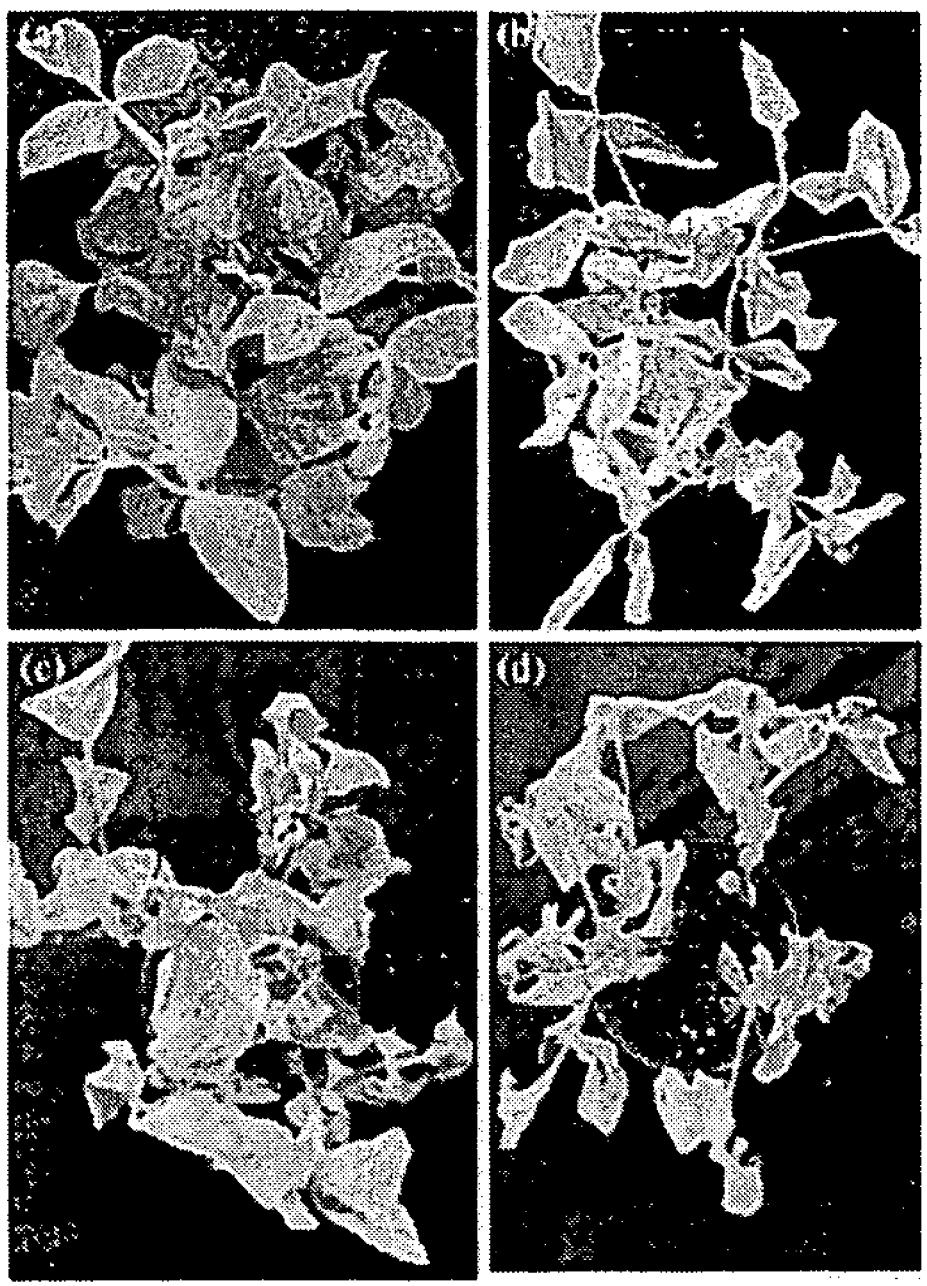
FIG. 5 shows herbicide resistance in soybean conferred by infection with the BPMV vector expressing the bar gene. Soybean seedlings were inoculated onto the primary leaves with either wild-type virus, transcripts from the BPMV-bar construct, transcripts from the BPMV-GFP construct, or mock-inoculated with buffer alone. The herbicide treatment (0.1% amino glufosinate in deionized water) was applied to all plants when the second trifoliolate leaves were fully expanded. Photographs were taken 20 days after the herbicide treatment. Soybean plants infected with: BPMV-bar construct (FIG. 5A); mock-inoculated control (FIG. 5B); wild-type BPMV strain K-G7 (FIG. 5C); and BPMV-GFP construct (FIG. 5D) are shown.
Figure 6:
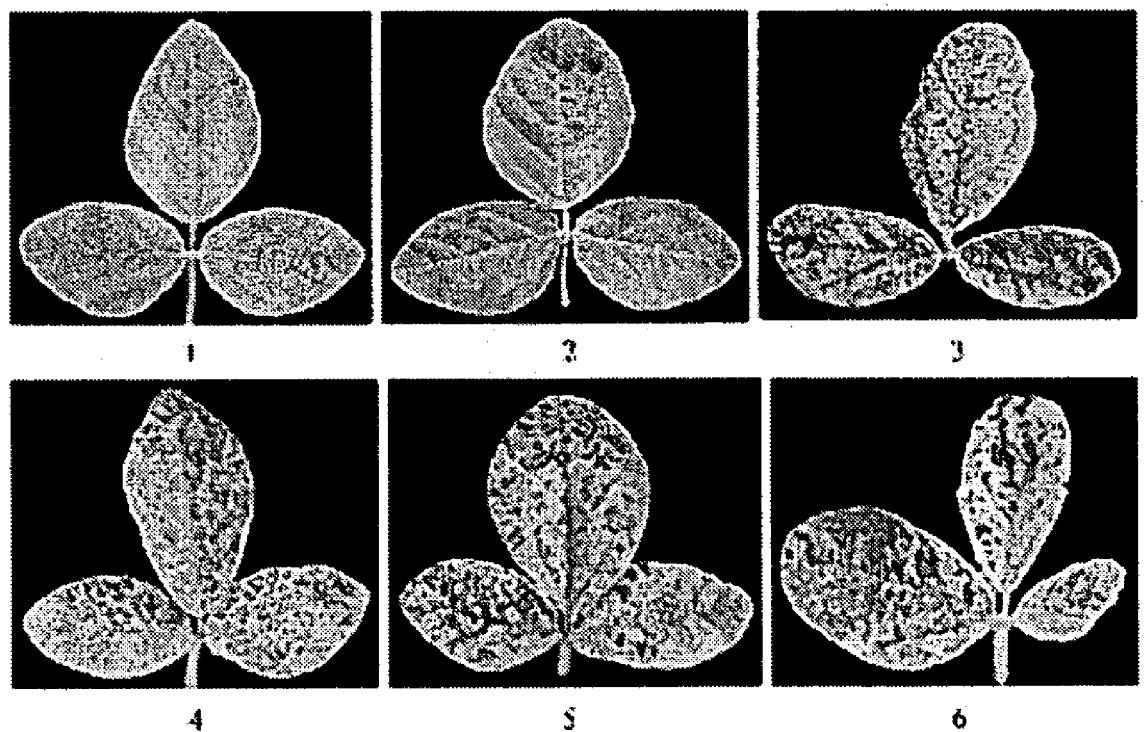
FIG. 6 shows enhancement of symptom severity in soybean plants infected with the BPMV vector carrying known viral suppressors of RNA silencing. Photographs of first trifoliolate leaves from soybean plants inoculated with leaf extracts from plants infected with transcripts from pGHoR1 plus transcripts from: pGG7R2 (panel 2); pGG7R2-P19 (panel 3); pGG7R2-TCVCP (panel 4); pGG7R2-HCPro(S7) (panel 5); or pGG7R2-HCPro(T) (panel 6) are shown. A mock-inoculated control plant is shown in panel 1. Note enhanced symptom severity including necrosis on soybean plants infected with BPMV constructs carrying suppressors of RNA silencing (panels 3-6). The photographs were taken 2 weeks postinoculation.
Figure 7:
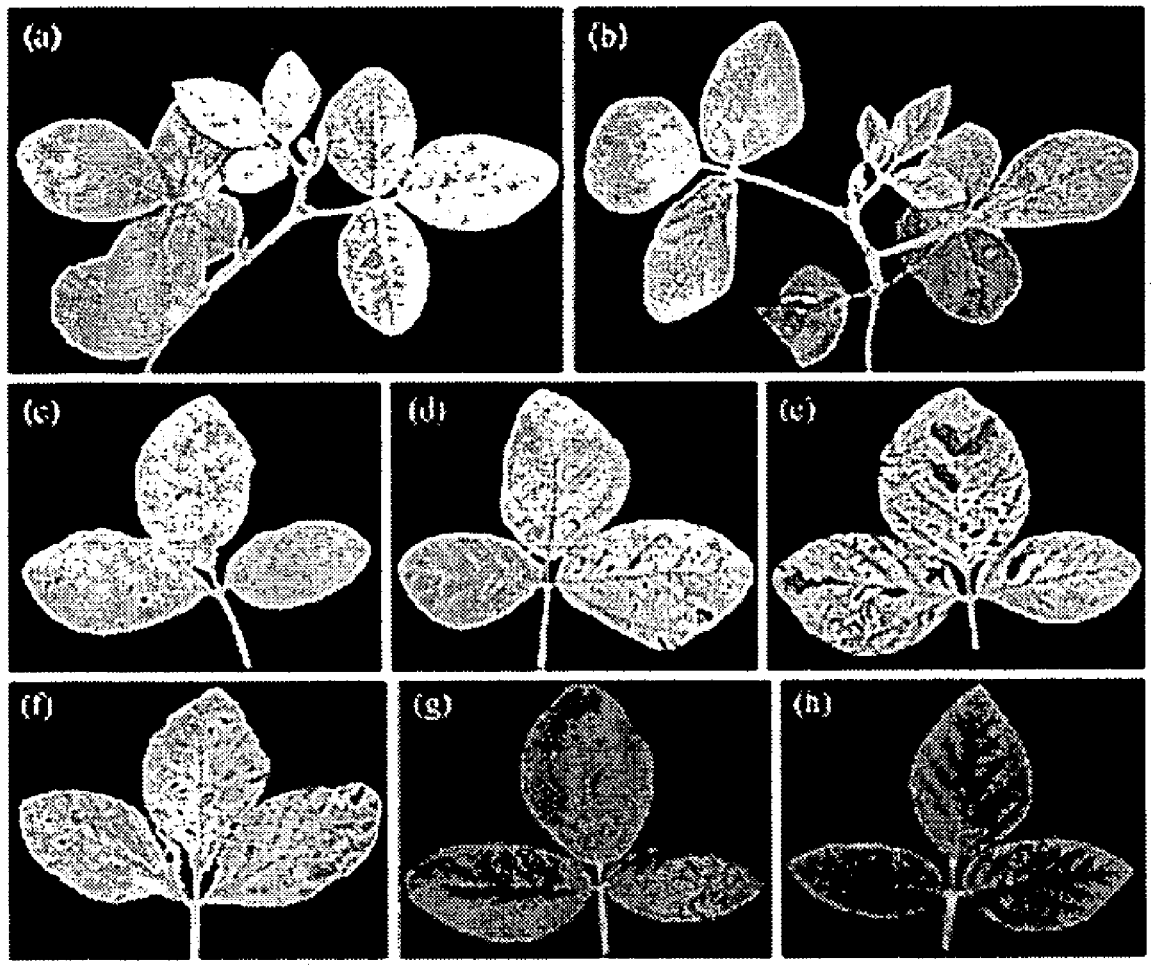
FIG. 7 shows virus-induced gene silencing (VIGS) of the soybean PDS gene.

Plants infected with the BPMV-bar construct were resistant to ammoniumglufosinate when applied as a 0.1 % solution (w/v) in deionized water (FIG. 5A). In contrast, the noninoculated control, BPMV K-G7-infected plants, and plants infected with the BPMV-GFP construct were killed within 3 weeks after herbicide treatment (FIG. 5). Furthermore, plants infected with BPMV-bar construct were found to withstand ammonium glufosinate treatment at a concentration of 1% (w/v) in deionized water with little or no damage.

It is known that certain RNA silencing suppressors encoded by plant viruses may enhance symptom severity induced by heterologous viruses (Pruss et al., *Plant Cells* 9:859-868 (1997); Yang and Ravelonandro, *Arch. Virol.* 147: 2301-2312 (2002)). Three different viral RNA silencing suppressors (TBSV-P19, TCV-CP, SMV-HC-Pro) with apparently dissimilar underlying mechanisms (Roth et al., *Virus Res.* 102:97-108 (2004)) were cloned into the BPMV vector and tested for their activity in soybean. The resulting constructs were infectious, and the infected plants showed very severe symptoms including extensive stunting, leaf deformation, blistering, and veinal necrosis compared with the relatively mild mottling symptoms induced by infections involving wild-type BPMV RNA2 (FIG. 6). The severe symptoms induced by these constructs are reminiscent of the top necrosis syndrome induced by double infection of soybean plants with BPMV and SMV (Anjos et al., *Phytopathology* 82:1022-1027 (1992)).

EXAMPLE VI

Silencing of Phytoene Desaturase in Soybean

Virus-induced gene silencing (VIGS) is an attractive tool for studies of gene function. To determine whether a VIGS vector based on BPMV could be useful in silencing of endogenous soybean genes, a 318 bp fragment of the phytoene desaturase (PDS) gene, which is necessary for production of carotenoid pigment production, was inserted into the BPMV vector, and the resulting construct was used to infect soybean. Soybean plants inoculated with the recombinant BPMV-PDS developed typical photobleached leaves 2 weeks postinoculation, indicating that the PDS gene had been silenced (FIG. 7*a*). The BPMVPDS vector was stable when leaf extracts were prepared from the upper leaves and used to inoculate a second set of healthy soybean seedlings. Representative upper leaves harvested at 21 dpi from the second passage plants are shown in FIG. 7. VIGS of the PDS gene was clearly evident regardless of the source of RNA1 (whether from the mild strain K-Ha1 or the severe strain K-Ho1) or the soybean cultivar used, Essex, Clark, Williams, or York.

Expression of RNA silencing suppressors from recombinant BPMV vectors showed significant enhancement in symptom severity (FIG. 6) and in the accumulation of the viral coat proteins, as assessed by immunoblot analysis and ELISA for soybean plants infected with the BPMV-HC-Pro construct. The enhancement in symptom severity and BPMV accumulation in soybean plants infected with BPMVHC-Pro construct is reminiscent of dual infection of soybean with BPMV and SMV (Anjos et al., *Phytopathology* 82:1022-1027 (1992)) and is consistent with the idea that BPMV does not effectively suppress RNA silencing (Gu, et al., *Virology* 333:271-283 (2005)). Expression of RNA silencing suppressors in combination with recombinant BPMV vectors may be useful for enhancing foreign protein expression levels (Mallory, et al., *Nat. Biotechnol* 20:622-625 (2002); Voinnet, *Plant J.* 33:949-956 (2003)). Although expression of more than one product (suppressor plus the proteins of interest) from the same BPMV vector is theoretically feasible (upper limit for insert size is 2.4 kbp), stability might be a concern because of the additional duplicated cleavage sites. Thus, expression of RNA silencing suppressors from co-infecting recombinant BPMV vector is probably a better approach.

Throughout this application various publications have been referenced. The disclosures of these publications in their entireties are hereby incorporated by reference in this application in order to more fully describe the state of the art to which this invention pertains. Although the invention has been described with reference to the exampled provided above, it should be understood that various modifications can be made without departing from the spirit of the invention.

What is claimed is:

1. A Bean pod mottle virus (BPMV) vector, comprising a nucleic acid sequence encoding an RNA2 polyprotein open reading frame (ORF), wherein said RNA2 polyprotein ORF comprises two QM cleavage sites located between the movement protein (MP) and large coat protein (L-CP), wherein both of QM cleavage sites encompass SEQ ID NO:1, and wherein a nucleic acid sequence encoding a heterologous polypeptide is inserted between the two OM sites.

2. The vector of claim 1, wherein each codon encoding each of said two QM cleavage sites differs between the nucleic acid sequences encoding each of said two cleavage sites.

3. The vector of claim 1, wherein said QM cleavage sites comprise 8 amino acids derived from the C-terminus of the MP and 19 amino acids derived from the L-CP of BPMV RNA2.

4. The vector of claim 1, wherein a nucleic acid sequence encoding a heterologous polypeptide is inserted between said first and second QM cleavage sites.

5. The vector of claim 1, wherein said vector contains restriction sites for insertion of a heterologous sequence between said QM cleavage sites.

6. A method for expressing a heterologous polypeptide in a soybean plant, comprising inoculating a soybean plant with Bean pod mottle virus (BPMV) RNA1 and recombinant RNA2, wherein said recombinant BPMV RNA2 comprises a nucleic acid sequence encoding an RNA2 polyprotein open reading frame (ORF),
wherein said RNA2 polyprotein ORF comprises two QM cleavage sites located between the movement protein (MP) and large coat protein (L-CP), wherein both of QM cleavage sites encompass SEQ ID NO: 1, and wherein a nucleic acid sequence encoding a heterologous polypeptide is inserted between two QM sites.

7. The method of claim 6, wherein said first and second QM cleavage sites are located between the movement protein (MP) and large coat protein (L-CP) encoded by said RNA2 polyprotein.

8. The method of claim 6, wherein each codon encoding each of said two QM cleavage sites differs between the nucleic acid sequences encoding each of said two cleavage sites.

9. The method of claim 8, wherein the amino acid sequences of said first and second QM cleavage sites are identical.

10. The method of claim 6, wherein said QM cleavage sites comprise 8 amino acids derived from the C-terminus of the MP and 19 amino acids derived from the L-CP of BPMV RNA2.

11. The method of claim 6, wherein said recombinant RNA2 contains restriction sites for inserting said nucleic acid sequence encoding a heterologous polypeptide between said first and second QM cleavage sites.

12. A method for virus-induced gene silencing in a soybean plant, comprising inoculating a soybean plant with Bean pod mottle virus (BPMV) RNA, wherein said BPMV RNA comprises a nucleic acid sequence encoding at least a portion of a gene endogenous to the soybean plants, wherein said nucleic acid sequence encoding at least a portion of an endogenous gene is encoded by an RNA2 polyprotein open reading frame (ORF), wherein said RNA2 polyprotein ORF comprises two QM cleavage sites located between the movement protein (MP) and large coat protein (L-CP), wherein both of QM cleavage sites encompass SEQ ID NO:1, and wherein a nucleic acid sequence encoding a heterologous polypeptide is inserted between two QM sites.

13. The method of claim 12, wherein said nucleic acid sequence encoding at least a portion of an endogenous gene is encoded by an RNA2 polyprotein open reading frame (ORF).

14. The method of claim 12, wherein said RNA2 polyprotein ORF comprises a first and second QM cleavage site, wherein the nucleic acid sequences encoding said first and second QM cleavage sites differ sufficiently to reduce homologous recombination between said QM cleavage site encoding nucleic acid sequences and wherein said nucleic acid sequence encoding at least a portion of an endogenous gene is inserted between said first and second QM cleavage sites.

15. The method of claim 12, wherein said first and second QM cleavage sites are located between the movement protein (MP) and large coat protein (L-CP) encoded by said RNA2 polyprotein.

16. The method of claim 12, wherein each codon encoding said QM cleavage site differs between the nucleic acid sequences encoding said first QM cleavage site and said second QM cleavage site.

17. The method of claim 16, wherein the amino acid sequences of said first and second QM cleavage sites are identical.

18. The method of claim 14, wherein said QM cleavage sites comprise 8 amino acids derived from the C-terminus of the MP and 19 amino acids derived from the L-CP of BPMV RNA2.

* * * * *

SEQUENCE LISTING

```
<160> NUMBER OF SEQ ID NOS: 28

<210> SEQ ID NO 1
<211> LENGTH: 27
<212> TYPE: PRT
<213> ORGANISM: Artificial Sequence
<220> FEATURE:
<223> OTHER INFORMATION: Chemically synthesized

<400> SEQUENCE: 1

Gln Tyr Asn Glu Val Gln Ala Gln Met Glu Thr Asn Leu Phe Lys Leu
1               5                   10                  15

Ser Leu Asp Asp Val Glu Thr Pro Lys Gly Ser
            20                  25

<210> SEQ ID NO 2
<211> LENGTH: 57
<212> TYPE: DNA
<213> ORGANISM: Artificial Sequence
<220> FEATURE:
<223> OTHER INFORMATION: Primer chemically synthesized

<400> SEQUENCE: 2
taatacgact cactatagta ttaaaatttt cataagattt gaaattttga taaaccg        57
```

<210> SEQ ID NO 3
<211> LENGTH: 46
<212> TYPE: DNA
<213> ORGANISM: Artificial Sequence
<220> FEATURE:
<223> OTHER INFORMATION: Primer chemically synthesized

<400> SEQUENCE: 3
ttccgcggcc gctatggccg acgtcgactt tttttttttt tttttt            46

<210> SEQ ID NO 4
<211> LENGTH: 27
<212> TYPE: DNA
<213> ORGANISM: Artificial Sequence
<220> FEATURE:
<223> OTHER INFORMATION: Primer chemically synthesized

<400> SEQUENCE: 4
ggacgtcgag actccaaaag gttccat                                 27

<210> SEQ ID NO 5
<211> LENGTH: 29
<212> TYPE: DNA
<213> ORGANISM: Artificial Sequence
<220> FEATURE:
<223> OTHER INFORMATION: Primer chemically synthesized

<400> SEQUENCE: 5
aatttaaata gatttgtttc catttgagc                               29

<210> SEQ ID NO 6
<211> LENGTH: 71
<212> TYPE: DNA
<213> ORGANISM: Artificial Sequence
<220> FEATURE:
<223> OTHER INFORMATION: Primer chemically synthesized

<400> SEQUENCE: 6
aatttaaatt gtctcttgat gatgttgaaa cacccaaagg atcaatgagt aaaggagaag    60
aacttttcac t                                                        71

<210> SEQ ID NO 7
<211> LENGTH: 90
<212> TYPE: DNA
<213> ORGANISM: Artificial Sequence
<220> FEATURE:
<223> OTHER INFORMATION: Primer chemically synthesized

<400> SEQUENCE: 7
ggacgtcgtc caatgaaagc ttaaacaagt tagtctccat ttgtgcttgc acctcgttat    60
attgtttgta tagttcatcc atgccatgtg                                    90

<210> SEQ ID NO 8
<211> LENGTH: 70
<212> TYPE: DNA
<213> ORGANISM: Artificial Sequence
<220> FEATURE:
<223> OTHER INFORMATION: Primer chemically synthesized

<400> SEQUENCE: 8
atttaaattg tctcttgatg atgttgaaac acccaaagga tcaatggcat cctctgaaga    60
tgttatcaag                                                          70

<210> SEQ ID NO 9
<211> LENGTH: 79
<212> TYPE: DNA
<213> ORGANISM: Artificial Sequence
<220> FEATURE:
<223> OTHER INFORMATION: Primer chemically synthesized

<400> SEQUENCE: 9
gacgtcgtcc aatgaaagct taaacaagtt agtctccatt tgtgcttgca cctcgttata    60
ttgggcgccg gtggagtgg                                                 79

<210> SEQ ID NO 10
<211> LENGTH: 35
<212> TYPE: DNA
<213> ORGANISM: Artificial Sequence
<220> FEATURE:
<223> OTHER INFORMATION: Primer chemically synthesized

<400> SEQUENCE: 10
aatttaaatt gtctcttgat gatgttgaaa caccc                               35

<210> SEQ ID NO 11
<211> LENGTH: 34
<212> TYPE: DNA
<213> ORGANISM: Artificial Sequence
<220> FEATURE:
<223> OTHER INFORMATION: Primer chemically synthesized

<400> SEQUENCE: 11
ttggccagga tcctttgggt gtttcaacat catc                                34

<210> SEQ ID NO 12
<211> LENGTH: 44
<212> TYPE: DNA
<213> ORGANISM: Artificial Sequence
<220> FEATURE:
<223> OTHER INFORMATION: Primer chemically synthesized

<400> SEQUENCE: 12
atcgatggcc acaatataac gaggtgcaag cccaaatgga gacc                     44

<210> SEQ ID NO 13
<211> LENGTH: 44
<212> TYPE: DNA
<213> ORGANISM: Artificial Sequence
<220> FEATURE:
<223> OTHER INFORMATION: Primer chemically synthesized

<400> SEQUENCE: 13
gacgtcgtcc aatgaaagct taaacaagtt ggtctccatt tggg                     44

<210> SEQ ID NO 14
<211> LENGTH: 29
<212> TYPE: DNA
<213> ORGANISM: Artificial Sequence
<220> FEATURE:
<223> OTHER INFORMATION: Primer chemically synthesized

<400> SEQUENCE: 14
ggatcctccc aaaatcctga agctcagtt                                      29

<210> SEQ ID NO 15
<211> LENGTH: 23
<212> TYPE: DNA
<213> ORGANISM: Artificial Sequence

```
<220> FEATURE:
<223> OTHER INFORMATION: Primer chemically synthesized

<400> SEQUENCE: 15
actgtcaaag atccaaaaga gtc                                              23

<210> SEQ ID NO 16
<211> LENGTH: 23
<212> TYPE: DNA
<213> ORGANISM: Artificial Sequence
<220> FEATURE:
<223> OTHER INFORMATION: Primer chemically synthesized

<400> SEQUENCE: 16
gactcttttg gatctttgac agt                                              23

<210> SEQ ID NO 17
<211> LENGTH: 31
<212> TYPE: DNA
<213> ORGANISM: Artificial Sequence
<220> FEATURE:
<223> OTHER INFORMATION: Primer chemically synthesized

<400> SEQUENCE: 17
tcatcctctg ttgcacgata tcaccaactc t                                     31

<210> SEQ ID NO 18
<211> LENGTH: 30
<212> TYPE: DNA
<213> ORGANISM: Artificial Sequence
<220> FEATURE:
<223> OTHER INFORMATION: Primer chemically synthesized

<400> SEQUENCE: 18
ggatccagcg acaaatcaat ctctgaggca                                       30

<210> SEQ ID NO 19
<211> LENGTH: 33
<212> TYPE: DNA
<213> ORGANISM: Artificial Sequence
<220> FEATURE:
<223> OTHER INFORMATION: Primer chemically synthesized

<400> SEQUENCE: 19
gatatctcca acattgtaag ttttcatttc gga                                   33

<210> SEQ ID NO 20
<211> LENGTH: 30
<212> TYPE: DNA
<213> ORGANISM: Artificial Sequence
<220> FEATURE:
<223> OTHER INFORMATION: Primer chemically synthesized

<400> SEQUENCE: 20
cgcggatcca tggaacgagc tatacaagga                                       30

<210> SEQ ID NO 21
<211> LENGTH: 32
<212> TYPE: DNA
<213> ORGANISM: Artificial Sequence
<220> FEATURE:
<223> OTHER INFORMATION: Primer chemically synthesized

<400> SEQUENCE: 21
tgtgttggcc actcgctttc tttttcgaag gt                                    32
```

```
<210> SEQ ID NO 22
<211> LENGTH: 30
<212> TYPE: DNA
<213> ORGANISM: Artificial Sequence
<220> FEATURE:
<223> OTHER INFORMATION: Primer chemically synthesized

<400> SEQUENCE: 22
cgcggatcca tggaaaatga tcctagagtc                                  30

<210> SEQ ID NO 23
<211> LENGTH: 34
<212> TYPE: DNA
<213> ORGANISM: Artificial Sequence
<220> FEATURE:
<223> OTHER INFORMATION: Primer chemically synthesized

<400> SEQUENCE: 23
attggatatc aatcctgagt gcttgccatt ttcc                             34

<210> SEQ ID NO 24
<211> LENGTH: 31
<212> TYPE: DNA
<213> ORGANISM: Artificial Sequence
<220> FEATURE:
<223> OTHER INFORMATION: Primer chemically synthesized

<400> SEQUENCE: 24
ccgcggatcc gccgcttgtg gctatatatc t                                31

<210> SEQ ID NO 25
<211> LENGTH: 31
<212> TYPE: DNA
<213> ORGANISM: Artificial Sequence
<220> FEATURE:
<223> OTHER INFORMATION: Primer chemically synthesized

<400> SEQUENCE: 25
cacagatatc tcctgcaccg gcaataacga t                                31

<210> SEQ ID NO 26
<211> LENGTH: 81
<212> TYPE: DNA
<213> ORGANISM: Artificial Sequence
<220> FEATURE:
<223> OTHER INFORMATION: Chemically synthesized

<400> SEQUENCE: 26
caatacaatg aagttcaagc tcaaatggaa acaaatctat tcaaattgtc tcttgatgat    60
gttgagactc caaaaggttc c                                             81

<210> SEQ ID NO 27
<211> LENGTH: 81
<212> TYPE: DNA
<213> ORGANISM: Artificial Sequence
<220> FEATURE:
<223> OTHER INFORMATION: Chemically synthesized

<400> SEQUENCE: 27
caatacaatg aagttcaagc tcaaatggaa acaaatctat ttaaattgtc tcttgatgat    60
gttgaaacac ccaaaggatc a                                             81

<210> SEQ ID NO 28
<211> LENGTH: 81
```

-continued

```
<212> TYPE: DNA
<213> ORGANISM: Artificial Sequence
<220> FEATURE:
<223> OTHER INFORMATION: Chemically synthesized

<400> SEQUENCE: 28
cagtataacg aggtgcaagc acaaatggag actaacttgt ttaagctttc attggacgac      60
gtcgagactc caaaaggttc c                                               81
```